United States Patent [19]

Kamatani et al.

[11] 4,013,509

[45] Mar. 22, 1977

[54] PRODUCTION OF L(+)-TARTARIC ACID

[75] Inventors: Yoshio Kamatani, Osaka; Hisayoshi Okazaki, Kyoto; Ko Imai, Osaka; Noriaki Fujita, Osaka; Yoshio Yamazaki, Osaka; Katsuhiko Ogino, Osaka, all of Japan

[73] Assignee: Takeda Chemical Industries, Ltd., Japan

[22] Filed: Jan. 19, 1976

[21] Appl. No.: 650,024

[30] Foreign Application Priority Data

Jan. 31, 1975 Japan .............................. 50-13737
May 7, 1975 Japan .............................. 50-54957

[52] U.S. Cl. .................................. 195/30; 195/114
[51] Int. Cl.² ........................................... C12D 1/02
[58] Field of Search ...................................... 195/30

[56] References Cited

OTHER PUBLICATIONS

Martin et al., J. of Bacteriology, vol. 70, pp. 405–414 (1955).

*Primary Examiner*—Alvin E. Tanenholtz
*Attorney, Agent, or Firm*—Wenderoth, Lind & Ponack

[57] ABSTRACT

Calcium cis-epoxysuccinate is converted into calcium L(+)-tartarate by a microorganism in a high concentration and is a better yield. This process is accelerated in the presence of a nonionic type surfactant of the medium.

7 Claims, No Drawings

PRODUCTION OF L(+)-TARTARIC ACID

This invention relates to a method for producing L(+)-tartaric acid. More concretely, this invention relates to an improved method for producing L(+)-tartaric acid, which comprises, in a process for the preparation of tartaric acid by microbiologically hydrolyzing epoxy-succinic acid, incorporating the calcium cis-epoxysuccinate as the raw material in the culture medium, incubating the microorganism and producing therewith the calcium L(+)-tartarate.

Hitherto, the method for producing meso-tartaric acid by microbiologically hydrolyzing the trans-epoxysuccinic acid has been publicly known (Journal of Bacteriology 70,405(1955)). Also, the present inventors had already completed the method for producing L(+)-tartaric acid by the microbiological hydrolysis of cis-epoxysuccinic acid; and with which filed an application for Japanese Patent (Application Ser. No. 8149/1975, filed on Jan. 17, 1975).

For the improvement of the above method, the inventors have made further deepened studies in the aspects of conditions of microbiological preparation of L(+)-tartaric acid from cis-epoxysuccinic acid, and have arrived at such findings that the solution of cis-epoxysuccinate, a starting material, has the property of inhibiting the growth of microorganisms; and said solution, when being in the concentration of more than 3–5%, is apt to cause remarkable delay of growth, or occasionally leads to entirely growth-prohibitive state of the microbes. Accordingly, it is difficult to feed a large amount of the salts of high solubility to water all at one time into the culture medium, for example, such salts as sodium, potassium, ammonium salt, or the like salts.

In contrast to the above, the calcium cis-epoxy succinate is of such low solubility to water as only 1% or so at room temperature, so that even if a mass of the calcium cis-epoxysuccinate is added altogether for once, there is neither observed the delay in growth of microbes in the culture, nor is observed any delay in hydrolysis.

In addition to the above, when the calcium cis-epoxysuccinate is used for the raw material to produce calcium L(+)-tartarate, the solubility of calcium L(+)-tartarate to water is so low that the reactant product is readily precipitated, which is removed outward of the reaction system quite easily. There occurs no more inhibition of hydrolysis due to reaction product, nor further decomposition of L(+)-tartaric acid due to microorganisms, and hence, the hydrolyzing reaction proceeds in a shorter time, thus ending in better yields.

On the other hand, directing our attention to the problem of material, it is found that cis-epoxysuccinic acid, which is the starting substance, is generally prepared by a conventional method which involves the oxidation of maleic acid in an aqueous solution by hydrogen peroxide in the presence of such catalysts as tungstic acid, molybdic acid, molybdenum or tungsten heteropoly-acid, or other salts of those acids; However, as an alternative method, such process is also feasible that maleic acid is subjected to epoxidation in the form of sodium, potassium, calcium and the like salts, and then followed by ion exchange or by addition of other metal salts, thereby effectively converting said maleic acid to the objective cis-epoxysuccinic acid or succinate. As above mentioned, there are various methods for preparing cis-epoxysuccinic acid. Of these methods, however, in the method which involves converting cis-epoxysuccinic acid to L(+)-tartaric acid by employing microorganisms, it is advisable that the raw material does not contain in it any such impurities resulting from epoxidation, as for example maleic acid, DL-tartaric acid, epoxidation catalyst and the like, because the presence of those impurities tends to induce the inhibition of the growth of microbes, or the inhibition of enzyme activity; and in the end, the purification procedures for the resultant L(+)-tartaric acid is rendered unduly complicated. Cis-epoxysuccinic acid and its salt of sodium, potassium and the like are of such a high solubility to water that the isolation of these from aqueous solution becomes complicated, whereas the calcium cis-epoxysuccinate, whether it be normal or acid salt, is of solubility low enough to be readily isolated from the aqueous solution. Therefore, the calcium cis-epoxysuccinate to be obtained through this method is advantageous in respect of high purity and good yield; and consequently, it does not contain any such impurities as would inhibit the growth of microorganism or enzyme activity, nor any impurities tending to complicate the purification procedures. For obtaining this calcium cis-epoxysuccinate, either of the following twofold methods is selectively applicable. In one way, the calcium maleate may be used as a raw material as above described, while in the other alternative way, epoxidation reaction may proceed in the form of maleic acid or its salts of sodium, potassium and the like; and after which the resultant product is isolated, or else, instead of resorting to isolation, conversion to calcium cis-epoxysuccinate may be carried out by adding calcium salt, calcium hydroxide, calcium oxide, and the like, thereby forming up such compound as calcium cis-epoxysuccinate. In the case where the calcium maleate is to be used for raw material, it is advantageous that firstly, epoxidation reaction is carried out by using the aqueous solution or slurry which contains 0.2–1 gram-atom of calcium to the amount of 1 mole of maleic acid; and secondly, after the reaction, calcium compound is to be added; or otherwise, instead of adding said calcium compound, the resultant product may be isolated in the form of such compounds as hydrogen-calcium cis-epoxysuccinate, or calcium cis-epoxysuccinate, or further, as the mixture of those compounds. Especially, when epoxidation reaction is proceeding by the use of an aqueous solution or slurry containing calcium of 0.4–0.8 gram-atom proportioned to the amount of 1 mole of maleic acid, high-purity calcium cis-epoxysuccinate can be obtained in good yield without requiring particular purification. Standing on the ground as above described, it can be concluded that, through the method involving the use of calcium cis-epoxysuccinate as the starting material, the chain of conversion starting from the raw material crystal to reach the crystal of calcium L(+)-tartarate, which is the resultant product, can be completed in high concentration, and in better yield, as well as in rapid velocity or processing; and in addition, isolation of the resultant product can be readily done. All of such advantages as above signify the competency as the industrialized manufacturing method for L(+)-tartaric acid.

As the second improvement to the method for producing L(+)-tartaric acid, the present inventors have found that upon using calcium cis-epoxysuccinate as the raw material, if nonionic type surfactant is present in the culture medium, the fermentation period is more remarkably curtailed, and the calcium cis-epoxysuccinate of high concentration can be converted into calcium L(+)-tartarate in a high efficiency.

Based on the above findings, research efforts have been further made, finally to culminate in the completion of the present invention.

Thus, the main object of the present invention is to provide an improved method for producing L(+)-tartaric acid in which the incubation of microorganism and the hydrolysis of calcium cis-epoxysuccinate into calcium L(+)-tartarate proceed simaltaneously.

The second object of the present invention is to provide an improved method for producing L(+)-tartaric acid in which the hydrolysis of calcium cis-epoxysuccinate to calcium L(+)-tartarate can be conducted in a high concentration of the material, in a better yield and in a shorter period.

Further objects will be explained in the following descriptions.

Thus, the present invention relates to an improved method for producing L(+)-tartaric acid which comprises; (1) incorporating the calcium cis-epoxysuccinate as the raw material in the culture medium; (2) incubating a microorganism which is capable of hydrolysing cis-epoxysuccinate to L(+)-tartaric acid; and thereby converting the calcium cis-epoxysuccinate into calcium L(+)-tartrate.

A further improved feature of the method comprises (1) incorporating a nonionic type surfactant, in combination with the calcium cis-epoxysuccinate, in the culture medium; (2) incubating such a microorganism; and (3) thereby converting the calcium cis-epoxysuccinate into the calcium L(+)-tartarate.

As for the microorganisms to be employed in this invention, any sort of microbe is employable as long as it is capable of hydrolyzing cis-epoxysuccinic acid and of forming L(+)-tartaric acid. For example, the below itemized ones may be employed i.e., *Acinetobacter tartarogenes* KB-82(IFO 13644; Ferm No. 2854; ATCC 31105); The same species KB-99 (IFO 13650; Ferm No. 2860; ATCC 31111); The same species KB-111 (IFO 13656; Ferm No. 2866; ATCC 31117); The same species KB-112 (IFO 13657; Ferm No. 2867; ATCC 31118); *Agrobacterium aureum* KB-91 (IFO 13647; Ferm No. 2857; ATCC 31108); *Agrobacterium viscosum* KB-105 (IFO 13652; Ferm No. 2862; ATCC 31113); *Rhizobium validum* KB-97(IFO 13648; Ferm No. 2858; ATCC 31109): The same species KB-106 (IFO 13653; Ferm No. 2863; ATCC 31114); *Pseudomonas species* KB-86(IFO 13645; Ferm No. 2855; ATCC 31106).

The particulars of the bacteriological characteristics of these microbes are described below:

1. Taxonomic properties of the strains KB-82, KB-99, KB-111, and KB-112.
    a. Cell morphology.
    1. Spherical rods, 0.8–1.0 by 1.0–1.3 $\mu$m.
    2. In youg cultures short rod cells and large irregular cells are found. In older cultures the cells are nearly spherical.
    3. Non-motile.
    4. Non-sporing.
    5. Gram-negative.
    6. Non-acid-fastness.
    b. Cultural characteristics.
    1. Nutrient agar plate: Circular, entire, convex, smooth, grayish white, opaque, glistening.
    2. Agar slant: Growth moderate, filiform, smooth, grayish white, glistening.
    3. Broth: Slightly turbid; no surface growth; sediment.
    4. Gelatin stab: No liquefaction.
    5. Litmus milk: Alkaline; no peptonization.
    c. Physiological properties.
    1. Nitrate reduction: KB-111 and KB-112 are positive but KB-82 and KB-99 are negative in nitrate broth.
    2. Denitrification does not occur.
    3. Methyl red test: negative.
    4. Acetylmethylcarbinol is not produced.
    5. Indole is not produced.
    6. Hydrogen sulfide is not produced.
    7. Starch is not hydrolized.
    8. Citrate is utilized.
    9. Nitrates and ammonium salts are utilized as nitrogen sources.
    10. Achromogenic.
    11. Urease is produced.
    12. Oxidase: positive.
    13. Catalase: positive.
    14. No growth at pH 4.5 and 8.6. Optimal pH, at about 7. No growth at 8° C and 40° C. Optimal temperature, at about 30° C.
    15. Aerobic.
    16. Hugh and Leifson test: oxidative.
    17. Acid but no gas from L-arabinose, D-xylose, and D-fructose. Slightly acid but no gas from D-glucose, D-mannose, D-galactose, and glycerol. No acid and no gas from maltose, lactose, trehalose, D-sorbitol, D-mannitol, inositol, and starch.
    d. Other taxonomic properties.
    1. Resistant to 5 units of penicillin.
    2. Isolated from soil.
2. Taxonomic properties of the strain KB-86.
    a. Cell morphology.
    1. Rods, 0.6–0.8 by 1.5–3.0 $\mu$m.
    2. Not pleomorphic.
    3. Motile by polar monotrichous flagellum.
    4. Non-sporing.
    5. Gram-negative.
    6. Non-acid-fastness.
    b. Cultural characteristics.
    1. Nutrient agar plate: Circular, entire, convex, smooth, translucent, creamy white, glistening.
    2. Agar slant: Growth moderate, filiform, smooth, creamy white, glistening.
    3. Broth: Slightly turbid; no surface growth; sediment.
    4. Gelatin stab: No liquefaction.
    5. Litmus milk: Unchanged.
    c. Physiological properties.
    1. Nitrates are not reduced in nitrate broth.
    2. Denitrification does not occur.
    3. Methyl red test is negative.
    4. Acetylmethylcarbinol is not produced.
    5. Indole is not produced.
    6. Hydrogen sulfide is not produced.
    7. Starch is not hydrolized.
    8. Citrate is utilized.
    9. Nitrates and ammonium salts are utilized as nitrogen sources.
    10. Water soluble pigments are not produced.
    11. Urease is produced.
    12. Oxidase: positive.
    13. Catalase: positive.

14. No growth at pH 6.0 and 10.5. Optimal pH, at about 7. No growth at 40° C. Growth at 10° C. Optimal temperature, between 25° C and 30° C.
15. Aerobic.
16. Hugh and Leifson test: oxidative.
17. Acid but no gas from L-arabinose, D-xylose, D-glucose, D-mannose, D-fructose, D-galactose, maltose, sucrose, trehalose, D-sorbitol, D-mannitol, and glycerol. No acid and no gas from lactose, inositol, and starch.
 d. Other taxonomic properties.
  1. Nitrogen fixation does not occur.
  2. Amino acids and vitamins are not necessary for growth.
  3. Isolated from soil.
3. Taxonomic properties of the strain KB-91.
 a. Cell morphology.
  1. Rods, 0.5–0.7 by 1.0–3.0 μm.
  2. Not pleomorphic.
  3. Motile by one to three peritrichous flagella.
  4. Non-sporing.
  5. Gram-negative.
  6. Non-acid-fastness.
 b. Cultural characteristics.
  1. Nutrient agar plate: Circular, spreading, convex, transparent, yellow, glistening.
  2. Agar slant: Growth moderate, spreading, smooth, yellow, glistening.
  3. Broth: Turbid; no surface growth; sediment.
  4. Gelatin stab: Stratiform liquefaction.
  5. Litmus milk: Neutral to slightly alkaline without serum zone. No peptonization. Grayish brown color after 2 weeks.
 c. Physiological properties.
  1. Nitrates are not reduced in nitrate broth.
  2. Dentrification does not occur.
  3. Methyl red test negative.
  4. Acetylmethylcarbinol is not produced.
  5. Indole is not produced.
  6. Hydrogen sulfide is not produced.
  7. Starch is not hydrolized.
  8. Citrate is utilized.
  9. Nitrates and ammonium salts are utilized as nitrogen sources.
  10. Chromogenic.
  11. Urease is produced.
  12. Oxidase: positive.
  13. Catalase: positive.
  14. No growth at pH 4.5 and 10.5. Optimal pH, at about 7. No growth at 40° C. Growth at 10° C. Optimal temperature, at about 30° C.
  15. Aerobic.
  16. Hugh and Leifson test: oxidative.
  17. Acid but no gas from L-arabinose, D-glucose, D-mannose, D-fructose, D-galactose, lactose, trehalose, D-sorbitol, D-mannitol, inositol. No acid and no gas from D-xylose, maltose, sucrose, glycerol, and starch.
 d. Other taxonomic properties.
  1. 3-Ketolactose production test: positive.
  2. Amino acids and vitamins are not necessary for growth.
  3. Growth on aniline blue glucose agar. Dye is not absorbed.
  4. Cellulose is not decomposed.
  5. Isolated from soil.
  6. Not parasitic for plants as checked.
4. Taxonomic properties of the strain KB-105.
 a. Cell morphology.
  1. Rods, 0.5–0.7 by 1.0–3.0 μm.
  2. Not pleomorphic.
  3. Motile by one to three peritrichous flagella.
  4. Non-sporing.
  5. Gram-negative.
 b. Cultural characteristics.
  1. Nutrient agar plate: Circular, entire, convex, smooth, opaque, yellowish white, glistening.
  2. Agar slant: Growth moderate, filiform, yellowish white, glistening.
  3. Broth: Sediment, pellicle.
  4. Gelatin stab: No liquefaction.
  5. Litmus milk: Alkaline with serum zone.
 c. Physiological properties.
  1. Nitrates are not reduced in nitrate broth.
  2. Denitrification does not occur.
  3. Methyl red test: negative.
  4. Acetylmethylcarbinol is not produced.
  5. Indole is not produced.
  6. Hydrogen sulfide is not produced.
  7. Starch is not hydrolized.
  8. Citrate is utilized in Christensen's medium but not in Koser's medium.
  9. Nitrates and ammonium salts are utilized as nitrogen sources.
  10. Achromogenic.
  11. Urease is produced.
  12. Oxidase: positive.
  13. Catalase: positive.
  14. No growth at pH 4.5 and 10.5. Optimal pH, at about 7. No growth at 40° C. Growth at 10° C. Optimal temperature, at about 30° C.
  15. Aerobic.
  16. Hugh and Leifson test: oxidative.
  17. Acid but no gas from L-arabinose, D-xylose, D-glucose, D-mannose, D-fructose, D-galactose, maltose, sucrose, trehalose, D-sorbitol, D-mannitol, and glycerol, No acid and no gas from lactose, inositol, and starch.
 d. Other taxonomic properties.
  1. 3-Ketolactose production test: positive.
  2. Vitamin necessary for growth.
  3. Growth on aniline blue glucose agar. Dye is not absorbed.
  4. Viscous colonies are formed on sugar media.
  5. Cellulose is not decomposed.
  6. Isolated from soil.
  7. Not parasitic for plants as checked.
5. Taxonomic properties of the strains KB-97 and KB-106.
 a. Cell morphology.
  1. Short rods, 0.8–1.0 by 1.0–1.5 μm.
  2. In young cultures large irregular cells are found. In older cultures the cells become coccoid rods.
  3. Non-motile.
  4. Non-sporing.
  5. Gram-negative.
  6. Non-acid-fastness.
 b. Cultural characteristics.
  1. Nutrient agar plate: Circular, entire, convex, smooth, grayish white, opaque, glistening.
  2. Agar slant: Growth moderate, filiform, smooth, grayish white, glistening.
  3. Broth: Slightly turbid; no surface growth; sediment.
  4. Gelatin stab: No liquefaction.

5. Litmus milk: Slightly alkaline; not peptonized; no serum zone.

c. Physiological properties.
1. Nitrate reduction: KB-106 is positive but KB-97 is negative in nitrate broth.
2. Denitrification does not occur.
3. Methyl red test: negative.
4. Acetylmethylcarbinol is not produced.
5. Indole is not produced.
6. Hydrogen sulfide is not produced.
7. Starch is not hydrolized.
8. Citrate is not utilized.
9. Nitrates and ammonium salts are utilized as nitrogen sources.
10. Achromogenic.
11. Urease is produced.
12. Oxidase: positive.
13. Catalase: positive.
14. No growth at pH 4.5 and 8.6. Optimal pH, at about 7. No growth at 40° C. Growth at 10° C. Optimal temperature, at about 30° C.
15. Aerobic.
16. Hugh and Leifson test: oxidative.
17. Acid but no gas from L-arabinose, and D-fructose. Slightly acid but no gas from D-xylose, D-glucose, D-mannose, D-galactose, and glycerol. No acid and no gas from maltose, sucrose, lactose, trehalose, D-sorbitol, D-mannitol, inositol, and starch.

d. Other taxonomic properties.
1. 3-Ketolactose is not produced.
2. Growth on yeast extract media within 3 days.
3. Isolated from root nodules of clover.

The method of the present invention is carried out by adding calcium cis-epoxysuccinate into the culture medium, in the course of microbe-incubation process, thereby making it possible to perform the simultaneous and paralleled actions of microbe-incubation and chemical reaction.

Upon practicing the incubation work for the microbes, the culture medium may be either in liquid state or solid state; but commonly applicable as well as more convenient way is to resort to shaking culture, or aerated agitation culture, which are based on the liquid culture medium.

There is no particular limitation or restrictive conditions in determining the state of the culture medium, that is, any sort of culture medium may be employed to the extent that the culture medium can accommodate said microbes, allowing them to grow up normally and securely, and also that the enzyme system which is capable of converting the calcium cis-epoxysuccinate into calcium L(+)-tartarate can be properly formed therein. For example, as the carbon source, calcium cis-epoxysuccinate, glucose, lactose, glycerin, sucrose (i.e., succharose), molasses, organic acids, hydrocarbons, and the like, may be used; and as the nitrogen source, there may be designated as examples such hydrolysate of protein as peptone, protein hydrolyzate, e.g. casamino acid (manufactured by Difco) and N-Z-Amine (manufactured by Schefield), along with such substances as yeast extract, soy bean cakes, corn steep liquor, amino acids, various kinds of ammonium salts, various kinds of nitrates, and other organic, or inorganic nitrogen compounds, all of the above being validly applicable. Further, as the inorganic salts, various kinds of phosphates, magnesium sulfate, sodium chloride, and the like, may be added as the pertinent additives; and also, for the purpose of encouraging the growth of bacteria, various kinds of vitamins, compounds associated with nucleic acid, etc., may be added. Whatever incubating method may be adopted for the actual working occasions, it is recommendable to add, at the starting time of incubation of cultivating, cis-epoxysuccinate into the culture medium, even if in small amount, in that it is efficacious to yield better results.

Again, when setting out on the incubation work, it is pre-erable to inoculate the culture medium with some proper amount of culture broth which may be obtained through the pre-culturing which has been done beforehand on a small scale.

The incubating conditions, involving culturing temperature, duration of culturing time, acidity-alkalinity of liquids prevalent in the culture medium, and the like factors, are subject to variation according to the kind of microorganisms employed, or to the composition and elements of the culture medium. However, if only adequate selection and adjustment are done simply aiming at the ultimate target of maximum yields of said enzyme system, it would justify and suffice the objective of the work. In many cases of practice, good result can be obtained by making incubation under aerobic condition, at around 20°–40° C, and for 1–7 days, meanwhile maintaining culture medium at around pH 5–9.

As the starting raw material, calcium cis-epoxysuccinate may be in whichever state of normal salt, acid salt or the mixture of them; but in the case of employing the raw material which contains an acid salt, it is commonly a favored practive to neutralize beforehand by calcium chloride, calcium carbonate and the like. Such a converting process is also feasible that sodium cis-epoxysuccinate, potassium cis-epoxysuccinate and the like be added to the reaction mixture containing the calcium chloride or other calcium salts which are equimolar as compared to said succinates, thereby making it possible to convert the succinates to the corresponding calcium salts.

On the occasion when the raw material, i.e., calcium cis-epoxysuccinate is added to the culture medium in the course of incubating process, the addition is generally conducted either prior to the starting time of incubation, or at an adequate time during the incubation. In this instance, the said material is to be made into, for example, the form of crystals of calcium salt, or else, into the form of a suspension in a proper solvent such as water; and said crystals or suspension is to be added all at one time, or continuously ranging over a given period of time, or intermittently at regular intervals during the incubation period of the microorganism.

The total amount of calcium cis-epoxysuccinate employable during the incubation of microorganisms may be not less than 5% (weight/volume) and it is possible to raise the amount up to as high as 50% (as free acid).

As the preferred embodiment of the present method a nonionic type surfactant is added into the culture medium to curtail the incubation period and to convert the calcium cis-epoxysuccinate to calcium L(+)-tartarate effectively.

As for the nonionic surfactant to be employed in the method of this invention, there are a wide range of applicable ones, which are effectively used, such as sorbitan fatty ester (e.g., sorbitan monooleate, sorbitan trioleate, and the like); polyoxyethylene sorbitan fatty ester (e.g., polyoxyethylene sorbitan monolaurate, polyoxyethylene sorbitan monooleate, and the like);

polyoxyethylene sorbitol fatty ester (e.g., polyoxyethylene sorbitol monolaurate, and the like); polyoxyethylene fatty ester (e.g., polyoxyethylene stearate, polyoxyethylene laurate, and the like); polyoxyethylene higher alcohol ether (e.g., polyoxyethylene lauryl alcohol ether, polyoxyethylene oleyl alcohol ether); polyoxyethylene alkyl aryl ether (e.g., polyoxyethylene nonyl phenol ether, polyoxyethylene octyl phenol ether, and the like); glyceryl fatty ester (e.g., glyceryl monostearate, and the like); alkylene glycol fatty ester (e.g., propylene glycol monostearate, and the like); polyoxypropylene polyoxyethylene alkyl ether (e.g., polyoxypropylene polyoxyethylene cetyl alcohol ether, and the like); polyoxyethylene alkyl phenol-formaldehyde condensation derivative (e.g., polyoxyethylene nonyl phenol-formaldehyde resin, polyoxyethylene octyl phenol-formaldehyde resin, and the like); polyoxyethylene alkyl amine or amide (e.g., polyoxyethylene oleyl amine, polyoxyethylene oleyl amide, and the like); polyoxyethylene lanolin derivative; polyoxyethylene lanolin alcohol derivative; polyoxyethylene sorbitol bees wax derivative; polyoxyethylene castor oil derivative; polyoxyethylene polyol; polyoxypropylene polyol; polyoxyethylene oxypropylene polyol (e.g., ethylene diamine oxypropylene oxyethylene tetraol, and the like); polyoxyethylene tetrahydrofurfuryl alcohol; polyoxypropylene fatty ester; or the likes.

In ordinary cases, the surface active agents are used within the concentration range of 0.05–5.0%, (weight/volume) and more preferably at around 0.05–2.0%. And, addition of the total amount of surface active agents may be effected all at one time before starting the incubation, or fractionally in the course of the incubation.

As have been described above, calcium L(+)-tartarate having been formed in the culture broth or in the reaction medium can be readily recovered by means of filtration or centrifugation.

While the preferred embodiments of the method of this invention are shown in the following examples, it is to be construed that the following examples are described for illustrating purposes only, and it will be obvious that the methods particularly described in the following examples are not to be construed as limitations of the content of this invention.

EXAMPLE 1

Strains of such species as *Acinatobacter tartarogenes* KB-82, *Pseudomonas species* KB-86, *Agrobacterium aureum* KB-91, and *Rhizobium validum* KB-106, are respectively used to inoculate 30 ml of culture contained in Erlenmeyer flask of 200 ml -capacity medium composed of casamino acid (0.05%), sodium nitrate (0.5%), dipotassium hydrogen phosphate (0.1%), magnesium sulfate (0.05%), ferrous sulfate (0.001%), pH 7.0; and simultaneously, the crystals of calcium-,disodium-, and dipotassium-cis-epoxysuccinate are added in such way that the respective final concentration may come up to 5% as the free acid each individually; and then the above mixture is subjected to rotatary-shaking culture at 30° C for 2 days. Centrifugal separation of the end-product is, when the culture broth is set up by the addition of calcium cis-epoxysuccinate, conducted after the calcium salt has been solubilized in advance with sulfuric acid. When the dipotassium salt or disodium salt is employed for setting up the culture broth, the culture broth is subjected to centrifugal separation without any preliminary treatment. The quantity of L(+)-tartaric acid was determined from the optical rotation value at 436 m$\mu$, whereas the cis-epoxysuccinic acid remaining unreacted was determined by Payne & Williams Method (G. B. Payne and P. H. Williams, Journal of Organic Chemistry 24, 54, (1959)). The results turned out as follows:

| Specific Strains | Cis-epoxysuccinic acid | | | | | |
|---|---|---|---|---|---|---|
| | Calcium salt | | Sodium salt | | Potassium salt | |
| | (A)* (%) | (B)** (%) | (A) (%) | (B) (%) | (A) (%) | (B) (%) |
| *Acinetobacter tartarogenes* KB-82 | 90 | 0 | 10 | 85 | 9 | 87 |
| *Pseudomonas species* KB-86 | 55 | 42 | 3 | 95 | 4 | 92 |
| *Agrobacterium aureum* KB-91 | 75 | 22 | 5 | 92 | 3 | 92 |
| *Rhizobium validum* KB-106 | 93 | 0 | 13 | 83 | 11 | 85 |

INDEXES:
*(A) Mole yield of the formed L(+)-tartaric acid. 100 % represents the case where all of cis-epoxysuccnic acid is completely converted to L(+)-tartaric acid.
**(B) Rate of remainder of the cis-epoxysuccinic acid as added. 100 % represents the case where 1.5 g of cis-epoxysuccinic acid remains as free acid.

EXAMPLE 2

A strain of *Acinetobacter tartarogenes* KB-111 is used to inoculate 500 ml of liquid culture medium contained in Sakaguchi flask of 2 l-capacity, composed of calcium cis-epoxysuccinate (0.6%), ammonium sulfate (0.5%), dipotassium hydrogen phosphate (0.1%), magnesium sulfate (0.05%), pH 7.0: and then, the above mixture is subjected to reciprocating-shaking culture at 30° C for 24 hours, and obtained as the result 500 ml of culture broth. This culture broth is transferred to a tank of 50 l-capacity which contains 30 l of liquid culture medium as composed of polypeptone (0.1%), ammonium sulfate (0.5%), dipotassium phosphate (0.1%), magnesium sulfate (0.05%), ferrous sulfate (0.001%), glucose (0.2%), pH 7.0; and at the same time, 180 g of calcium cis-epoxysuccinate is added. The resulting product is subjected to aerated agitation culture at 30° C, meanwhile around 20 g of Actocol 31-56 (product of Takeda Chemical Industry Ltd. in Japan) is added as the defoaming agent. When 24 hours have elapsed after the starting of the cultivation, 3 kg. (counted as free acid) of calcium cis-epoxysuccinate is added, followed by further cultivation for 48 hours. Around 30 l of the culture broth obtained is subjected to filtration with a filter press, and the solid part obtained is washed with water.

The centrifugation and washing are repeated and the solid parts obtained are triturated well and dried up. Having undergone all the above procedures, crystals of calcium L(+)-tartarate are obtained which comes up to an amount of 4.2 kg (as converted into anhydride; purity: 99%) (When calculated by the method of Example 1(A), the yield rate comes to 93%).

By way of a contrast with the above example, here is described another experiment, in which the same species of strain, i.e., KB-111, is used. In this experiment, the cultivation is carried out under the self-same terms and conditions as the preceeding example, only except for the material which is used, that is, instead of using the calcium cis-epoxysuccinate, disodium cis-epoxysuccinate of equal mole is employed in this latter example. Around 30 l of culture broth which has been obtained is filtered by means of the filter press. While the filtrate is being agitated well, 3.5 kg of the crystals of calcium chloride (dihydrate) is to be added by piecemeal; and the precipitates formed therein are collected by filtration through the filter press, thus gaining 5.8 kg of solid substance. By means of the thin-layer chromatogram of the said solid substance, there can be observed the remainder of cis-epoxysuccinic acid (Thin-Layer: Fine crystal cellulose Spot Film, produced by Tokyo Kasei Chemical Ind. Co. Solvent: Isopropyl Ether-Tetrahydrofuran-Formic Acid-Water (10:10:5:4). Developed with Brom Cresol Green). As based on the above findings, the quantity of L(+)-tartaric acid content is measured for determination, by the method shown in Example 1, i.e., by the method of optical rotation. As the final result of the above, it is found that the amount of the formed L(+)-tartaric acid is 1.3 kg as an anhydrous calcium salt (when calculated by the method of Example 1(A), the yield comes to 30%.

EXAMPLE 3

A strain of *Acinetobacter tartarogenes* KB-112 is used to inoculate 500 ml each of liquid culture media, respectively contained in two sets of Sakaguchi Flask of 2 l-capacity, composed of calcium cis-epoxy-succinate (0.6%), casamino acid (0.2%), ammonium nitrate (0.5%), dipotassium hydrogen phosphate (0.1%), magnesium sulfate (0.05%), pH 7.0; and this mixture is subjected to reciprocating-shaking culture at 30° C for 30 hours, thus producing 1 l of culture broth. This culture broth is transferred to a tank of 50 l-capacity which contains 30 l of liquid culture medium being composed of casamino acid (0.1%), ammonium nitrate (0.5%), dipotassium phosphate (0.1%), magnesium sulfate (0.05%), pH 7.0; and at the same time, calcium cis-epoxysuccinate is to be added in such way that it may become 9 kg as a free acid. After the addition of the above succinate, aerated agitation culture is carried out at 30° C for 3 days, meanwhile around 20 g of Actocol 31–56 as defoaming agent being added by piecemeal throughout the cultivating period. Around 38 l of the obtained culture broth is filtered with filter press. After washing, the solid part is suspended in 40 l of water and is stirred well. The result is left standing in order to have the solid part sedimented. After around 25 l of supernatant part is discarded, again 25 l of water is added and agitated; and the result is subjected to filtration through the filter press. The solid substance obtained therefrom is substantially crushed, triturated, and dried up. As the outcome of all the above, 11.9 kg. of the crystal of calcium L(+)-tartarate is obtained (as converted into anhydride purity: 98%).

EXAMPLE 4

A strain of *Rhizobium validum* KB 97 is used to inoculate 500 ml of liquid culture medium, contained in Sakaguchi flask of 2 l capacity, composed of yeast extract (0.5%), glucose (0.5%), pH 7.0. The above culture medium is subjected to reciprocating-shaking culture at 30° C for 24 hours; and culture broth obtained therefrom is transferred to a tank of 50 l-capacity which contains 30 l of liquid culture medium which is composed of corn steep liquor (0.2%), calcium cis-epoxysuccinate (0.6%), ammonium sulfate (0.6%), dipotassium hydrogen phosphate (0.1%), magnesium sulfate (0.03%), pH 7.0. The content in the tank is subjected to aerated agitation culture at 30° C for 40 hours, thereby obtaining around 30 l of culture broth. An amount of 15 l of this culture broth is again transferred to the tank of 200 l-capacity which contains 100 l of liquid culture medium being composed of corn steep liquor (0.05%), ammonium sulfate (1.0%), dipotassium hydrogen phosphate (0.1%), magnesium sulfate (0.5%), ferrous sulfate (0.001%), pH 7.0; and at the same time, calcium cis-epoxysuccinate is added in such way that it may come up to 10 kg as the free acid. After the addition of the above succinate, the content in the tank is subjected to aerated agitation culture at 30° C, meanwhile around 50 g of Actocol 31–56 as the defoaming agent being added. This aerated agitation cultivation is to last for 5 days; and during the period of 5 days, 20 kg each (counted as free acid) of calcium cis-epoxysuccinate is added on the first day and on the third day. Around 150 l of the culture broth obtained from the above setup is filtered with filter press; and after being washed, the solid part is suspended in 150 l of water. Subsequently, thorough agitation is exerted, to have said solid parts sedimented. Around 70 l of the supernatant part above the sedimentation is discarded; and again, around 70 l of water is added, then stirred well, and filtered through the filter press. The final yield of the crystals of calcium L(+)-tartarate is 64.8 kg. (purity: 99%), as the anhydride.

EXAMPLE 5

A strain of *Acinetobacter tartarogenes* KB-99 is used to inoculate 30 ml of liquid culture medium, contained in the Erlenmeyer flask of 200 ml capacity, composed of yeast extracts (0.5%), ammonium nitrate (0.5%), dipotassium hydrogen phosphate (0.1%), magnesium sulfate (0.05%), calcium chloride (dihydrate) (1.8%), pH 7.2; and in that case, the strain of 1 unit lot for Platinum Loop is to be inoculated every time. And, or the same time, sodium salt (A) or potassium salt (B) of cis-epoxysuccinic acid is to be added, in such way that either (A) or (B) may become 1.5 g as the free acids. The result of the above is subjected to rotary-shaking culture at 30° C for 2 days. A part from the above, another different stage of cultivation is set up, under the selfsame terms and conditions as above, but only except for such arrangements that (i) a modified culture medium is used, in which calcium chloride alone is eliminated from the above described culture medium; and (ii) after KB-99 strain is inoculated to such an amount as 1 unit lot of the platinum loop, calcium salt (C) of cis-epoxysuccinic acid is added in such way that it may become 1.5 g as the free acid. The culture broth thus obtained is filtered by means of glass filter, and then rinsed with water; and as the result, the crystals of L(+)-tartarate are recovered. The calcium L(+)-tartarate which is obtained from the culture broth of A, B and C are, as anhydrides respectively, 1.7 g., 1.8 g and 1.9 g; and as for purity, it is within the range of 97–99% common to all of them. Such an outcome significantly reveals an evidential fact that, even in the case the sodium salt or potassium salt of epoxysuccinic acid is used for the material, if only there is present, in the culture medium, the calcium ion which is almost equivalent to cis-epoxysuccinic acid in points of the amount, said material will readily react with said ion, thereby producing calcium salt of cis-epoxysuccinic acid; and hence, such consequence can be gained as is almost similar to the case where addition was made as the calcium salt initially from the starting point.

EXAMPLE 6

A strain of *Acinetobacter tartarogenes* KB-112 is used to inoculate 30 ml of culture medium, contained in the Erlenmeyer flask of 200 ml-capacity, which culture medium having been set up into such constitution that, to the basic culture medium which is composed of casamino acid (0.05%), ammonium nitrate (0.1%), dipotassium hydrogen phosphate (0.2%), magnesium sulfate (0.05%), ferrous sulfate (0.001%), pH 7.0, various sorts of nonionic surfactants are added so that the respective kinds of surface active agents may come to the concentration of 0.1%. And simultaneously, the crystals of calcium cis-epoxysuccinate is added, in such way that it may come to the final concentration of 40% counted as the free acid; and the above mixture is subjected to rotary shaken culture at 30° C, and for 2 days, and thence being allowed to exert reaction effect. After the termination of reactions, the liquid is filtered; and the crystals of filtrate obtained are solubilized by sulfuric acid. The solubilized crystals are then subjected to centrifugal separator to eliminate the solid substances. Subsequently, the quantitative determinations are made, with respect to L(+)-tartaric acid, by depending upon the optical rotation at 436 m$\mu$; and with respect to the remaining cis-epoxysuccinic acid, by using Payne & Williams Method (G. B. Payne and P. H. Williams: Journal of Organic Chemistry, 24, 54, (1959)). The results of determination turned out are shown in Table 1.

TABLE 1

| Description of (= 1) Surface Active Atents | Molar Yields (%)(= 2) of L(+)-tartaric acid | Rate of Residues (%)(= 3) of cis-epoxy-succinic acid |
|---|---|---|
| NIKKOL SR-10 | 45 | 52 |
| NIKKOL TO-10 | 72 | 25 |
| NIKKOL GS-6 | 50 | 48 |
| NIKKOL MYS-10 | 47 | 50 |
| NIKKOL BC-7 | 52 | 43 |
| NIKKOL NP-18TX | 55 | 40 |
| NIKKOL MGS-C | 48 | 47 |
| NIKKOL PMS-SE | 46 | 50 |
| NIKKOL TW-20 | 75 | 21 |
| NIKKOL BWA-20 | 74 | 21 |
| NIKKOL HCO-50 | 73 | 23 |
| NIKKOL R-1020 | 73 | 21 |
| NIKKOL TF-4 | 54 | 42 |
| NIKKOL TPMS-30 | 70 | 26 |
| TETRONIC T-702 | 52 | 45 |
| Not Added | 34 | 64 |

LEGEND
(= 1)The components of the Surface Active Agents used herein are as follows:
SR-10 : Sorbitan monooleate
TO-10 : Polyoxyethylene sorbitan monooleate
GS-6 : Polyoxyethylene sorbitol hexastearate
MYS-10 : Polyoxyethylene stearate
BC-7 : Polyoxyethylene cetyl alcohol ether
NP-18TX : Polyoxyethylene nonyl phenol ether
MGS-C : Glyceryl monostearate
PMS-SE : Propyleneglycol monostearate
TW-20 : Polyoxyethylene lanolin derivative
BWA-20 : Polyoxyethylene lanolin alcohol derivative
HCO-50 : Polyoxyethylene hardened castor oil derivative
R-1020 : Polyoxyethylene nonyl phenolformaldehyde resin
TF-4 : Polyoxyethylene tetrahydrofurfuryl alcohol
TPMS-30 : Polyoxyethylene oxypropylene stearate
All the above are the products manufactured by NIKKO CHEMICALS CO., LTD.
TETRONIC T 702 : Ethylenediamine polyoxypropylene oxyethylene tetraol (the product manufactured by ASAHI DENKA KOGYO CO.)
(= 2)100 % value represents the case where cis-epoxy-succinic acid has been completely converted to L(+)-tartaric acid.
(= 3)Rate of residues of the added cis-epoxysuccinic acid, in the crystals; and in which 100 % value represents the case where 12 g remains as free acid.

EXAMPLE 7

Strains of such species and numbers as *Acinetobacter tartarogenes* KB-82, *Pseudomonas species* KB-86, *Agrobacterium aureum* KB-91, *Acinetobacter tartarogenes* KB-99, *Agrobacterium viscosum* KB-105, and *Rhizobium validum* KB-106, are respectively used to inoculate 50 ml of liquid culture medium, contained in the Erlenmeyer flask of 200 ml-capacity, composed of corn steep liquor (0.2%), glucose (0.1%), ammonium nitrate (0.1%), dipotassium hydrogen phosphate (0.2%), magnesium sulfate (0.05%) and ferrous sulfate (0.001%), pH 7.0, and simultaneously, calcium cis-epoxysuccinate is added in such way that its final concentration may become 30% as the free acid, and thus the incubation is initiated. As are described in TABLE 2, various classes of surfactants are added at adequate timings; and the mixture is subjected to shaken culture at 30° C for 42 hours. From the result of cultivating, such a fact is observed that, with respect to each of the strains, the yield rates of L(+)-tartaric acid respectively show increased values as compared to the cases where just similar incubation is carried out without adding the surface active agent at all.

TABLE 2

| Strains | *(1) Concentration (%) of Surfactants when added | Time of Addition | *(2) Yield Rate (%) of L(+)-tartaric acid |
|---|---|---|---|
| *Acinetobacter tartarogenes* KB-82 | NONION LT-221 (0.2) | 0 | 83 |
|  | Not Added | — | 59 |
| *Pseudomonas species* KB-86 | NONION E-215 (0.05) | 0 | 47 |
|  | Not Added | — | 31 |
| *Agrobacterium aureum* KB-91 | NONION L-4 (0.1) | 12 | 65 |
|  | Not Added | — | 50 |
| *Acinetobacter tartarogenes* KB-99 | NIKKOL R-2030 (0.1) | 18 | 89 |
|  | Not Added | — | 77 |
| *Agrobacterium viscosum* KB-105*(3) | NIKKOL CO-60TX (0.05) | 0 | 59 |
|  | Not Added | — | 48 |
| *Rhizobium validum* KB-106 | PULRONIC (0.15) | 0 | 92 |
|  | Not Added | — | 85 |

LEGEND:
*(1)NINION LT-221 (Polyoxyethylene sorbitan monolaurate);
NONION E-215 (Polyoxyethylene oleyl ether);
NONION L-4 (Polyethylene glycol monolaurate).
[All of the above three are the products manufactured by NIPPON YUSHI CO. (Japan Fats & Oils Mfg. Co., Ltd.).]
NIKKOL R-2030 (Polyoxyethylene octyl phenolformaldehyde resin);
NIKKOL CO-60TX (Polyoxyethylene castor oil derivative); The above two are the products manufactured by NIKKO CHEMICALS CO., LTD.
PULRONIC L-61 (Polyoxyethylene oxypropylene polyol) [This is the product manufactured by ASAHI DENKA CO., LTD.]
*(2) Molar yield rate of L(+)-tartaric acid has been figured out by the same method as in Example 1.
*(3) In the case of this strain being incubated, 100 $\mu$g/ml of pyridoxal hydrochloride is added to the culture medium.

EXAMPLE 8

A strain of *Rhizobium validum* KB-97, together with a strain of *Acinetobacter tartarogenes* KB-111, are used to inoculate respectively 500 ml of culture medium, contained in Sakaguchi flask of 2 l-capacity, of such constitution that the surfactant is added to the basic culture medium which is just the same as the one in Example 1; and simultaneously, calcium cis-epoxysuccinate is added to the above in such a way that its final concentration may become 50% as the free acid. Subsequently, the above mixture is subjected to reciprocating shaken culture at 28° C. The quantity of cis-epoxysuccinic acid left over as residue in the culture broth is followed by means of the thin-layer chromatography (Thin-layer: fine-crystal cellulose spot film, as manufactured by TOKYO KASEI Co.; Solvent: isopropyl-ether-tetrahydrofuranformic acid - water (10:10:5:4); Color development: Brom-Cresol Green.)); and following the above, the incubation is continued until cis-epoxysuccinic acid disappears. Time elapsed during the converting reaction up until the end point of the reaction, along with the rate of yield of 1(+)-tartaric-acid forming (which is in molar yield figured out by the method used in Example 1), are indicated on TABLE 3, in which can be observed the curtailment of the reaction time and the increment in yield rate.

By way of contrasting with the above example, here is described another experiment, in which the same strain KB-97 is used. In this experiment, the cultivation and reaction are carried out under the self-same terms and conditions as the preceding example, only except that NIKKOL TW-20 (surfactant) alone is eliminated from the culture medium used in the preceding example. Around 40 l of the culture broth which is obtained from the above is purified by quite the same method as above. In the crystals obtained through the above purification, the residue of calcium cis-epoxysuccinate is confirmed to actually exist when tested by means of the thin-layer chromatography (carried out in compliance with the method used in Example 8); and therefore, the content of L(+)-tartaric acid is subjected to quantitative determination by the method of Example 6. As the

TABLE 3

| Strains | NONION OT-221* (0.15 %) | | RIPONOX NCG* (0.1 %) | | NIKKOL HCO-80* (0.2 %) | | Not Added | |
|---|---|---|---|---|---|---|---|---|
| | Time consumed (h) | Yield Rate (%) | Time consumed (h) | Yield Rate (%) | Time consumed (h) | Yield Rate (%) | Time consumed (h) | Yield Rate (%) |
| Rhizobium validum KB-97 | 84 | 89 | 96 | 89 | 78 | 92 | 108 | 85 |
| Acinetobacter tartarogenes KB-111 | 84 | 90 | 108 | 85 | 90 | 87 | 120 | 83 |

LEGEND:
*NONION OT-221: Polyoxyethylene sorbitan monooleate (manufactured by NIPPON YUSHI CO. - Japan Fats & Oils Mfg. Co.);
RIPONOX NCG: Polyoxyethylene alkyl phenol ether (manufactured by LION FATS & OILS MFG. CO.);
NIKKOL HCO-80: Polyoxyethylene hardened castor oil derivative (manufactured by NIKKO CHEMICALS CO.).

EXAMPLE 9

A strain of *Rhizobium validum* KB-97 is used to inoculate 500 ml of liquid culture medium which is contained in two sets of Sakaguchi flask of 2 l-capacity and composed of glucose (0.5%), corn steep liquor (1.0%), pH 7.0; and the contents of the respective flasks are subjected to reciprocating shaken culture at 28° C, and for 24 hours, thereby obtaining around 1 l of the culture broth. This culture broth is transferred to a tank of 50 l-capacity which contains 30 l of liquid culture medium which is composed of corn steep liquor (0.2%), ammonium nitrate (0.1%), dipotassium hydrogen phosphate (0.2%), magnesium sulfate (0.05%), ferrous sulfate (0.001%), and NIKKOL TW-20 (0.1%), pH 7.0; and at the same time, 6 kg. of calcium cis-epoxysuccinate is added counted as the free acid; and the resultant mixture is subjected to incubation at 30° C. After 19 hours has elapsed down from the starting time of incubation, 6 kg of calcium cis-epoxysuccinate is further added counted as the free acid; and the mixture is placed under continued incubation up to a point of totalled 48 solid hours down from the starting of the incubation. Subsequent series of treatments are such that around 40l of the obtained culture broth is filtered by means of the filter press; the solid part is rinsed with water; and is suspended in 30 l of water, which suspension is agitated thoroughly; after marking time to await precipitation of solid part, 20 l of supernatant part is discarded; 20 l of water is again added and stirred well; and the result is filtered with filter press, thus finally obtaining the crystals of calcium L(+)-tartarate. The quantity of this crystals is 15.9 kg. (purity: 98%) as anhydride.

result, it is found that the quantity of yield of the calcium L(+)-tartarate is equivalent to 12.3 kg as the anhydride.

EXAMPLE 10

A strain of *Rhizobium validum* KB-97 is used to inoculate 500 ml of a liquid culture medium (pH 7.0) contained in 2 l-capacity Sakaguchi flask, which is composed of corn steep liquor (2.0%), glucose (0.5%) and this liquid culture is incubated at 28° C, for 24 hours, under reciprocating-shaking culture. Thus obtained culture broth is transferred to a tank of 50 l-capacity which contains 30 l of the culture medium just self-same in composition as the one described above and the liquid culture medium in the said tank is subjected to incubation at 28° C for 24 hours under aerated agitation culturing. Around 15 l of the culture broth obtained therefrom is transferred into a tank of 200 l-capacity which contains 100 l of a liquid culture medium composed of corn steep liquor (0.5%), ammonium nitrate (0.1%), sodium dihydrogen phosphate (0.2%), magnesium sulfate (0.05%), ferrous sulfate (0.001%), polyoxyethylene lanolin derivative (0.1%) (pH 7.0) and simultaneously 40 kg of calcium cis-epoxysuccinate (as free acid) is added.

The whole is subjected to aerated agitation culturing at 30° C for 30 hours. The resultant cultured broth and the washing water of the tank, about 150l. in total are subjected to Decantor type centrifuge (Sumitomo Heavy Industries, Ltd. TS-210F type) to separate calcium L(+)-tartarate as crystals. The crystals are suspended in about 100l. of water. After sufficiently stirring, the crystals are separated by said decantor type centrifuge and again suspended in about 70l. of water and stirred well. The suspension is subjected to a filter-press to give 54 kg of calcium L(+)-tartarate (purity 98%) as anhydride.

What we claim is:

1. In a method for the preparation of tartaric acid by microbiologically hydrolyzing epoxysuccinic acid, an improved method for producing L(+)-tartaric acid, which comprises; (1) incorporating calcium cis-epoxysuccinate as a raw material in a culture medium; (2) incubating a microorganism which is capable of hydrolyzing cis-epoxysuccinic acid to L(+)-tartaric acid; and (3) thereby converting the calcium cis-epoxysuccinate into calcium L(+)-tartarate.

2. A method according to claim 1, wherein the final amount of the calcium cis-epoxysuccinate employed in the medium is not less than 5 percent (weight/volume) of the medium.

3. A method according to claim 1, wherein the final amount of the calcium cis-epoxysuccinate employed in the medium is not less than 30 percent (weight/volume) of the medium.

4. A method according to claim 1, wherein a nonionic type surfactant is incorporated in the culture medium.

5. A method according to claim 1, wherein the nonionic type surfactant is one selected from the group consisting of sorbitan fatty ester, polyoxyethylene sorbitan fatty ester, polyoxyethylene sorbitol fatty ester, polyoxyethylene fatty ester, polyoxyethylene higher alcohol ether, polyoxyethylene alkyl aryl ether, glycerol fatty ester, alkylene glycol fatty ester, polyoxypropylene polyoxyethylene alkyl ether, polyoxyethylene alkyl phenol-formaldehyde condensation derivative, polyoxyethylene alkyl amine or amide, polyoxyethylene lanolin derivative, polyoxyethylene lanolin alcohol derivative, polyoxyethylene sorbitol bees wax derivative, polyoxyethylene castor oil derivative, polyoxyethylene polyol, polyoxypropylene polyol, polyoxyethylene oxypropylene polyol, polyoxyethylene tetrahydrofurfuryl alcohol and polyoxypropylene fatty ester.

6. A method according to claim 1, wherein the concentration of nonionic type surfactant is 0.05–5.0% (weight per volume).

7. A method according to claim 1 wherein the microorganism is *Acinetobacter tartarogenes*, ATCC 31105, *Acinetobacter tartarogenes*, ATCC 31111, *Acinetobacter tartarogenes*, ATCC 31117, *Acinetobacter tartarogenes*, ATCC 31118, *Agrobacterium aureum*, ATCC 31108, *Agrobacterium viscosum*, ATCC 31113, *Rhozobium validum*, ATCC 31109, *Rhizobium validum*, ATCC 31114 and *Pseudomonas* species, KB-86, ATCC 31106.

* * * * *